(12) United States Patent
Musa

(10) Patent No.: US 6,716,992 B2
(45) Date of Patent: Apr. 6, 2004

(54) CYCLOALIPHATIC EPOXY COMPOUNDS CONTAINING STYRENIC, CINNAMYL, OR MALEIMIDE FUNCTIONALITY

(75) Inventor: Osama M. Musa, Hillsborough, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 65 days.

(21) Appl. No.: 10/201,373

(22) Filed: Jul. 22, 2002

(65) Prior Publication Data

US 2004/0014890 A1 Jan. 22, 2004

(51) Int. Cl.[7] .................. C07D 207/452; C07D 303/02; C07D 491/02
(52) U.S. Cl. ................. 548/453; 548/521; 549/546
(58) Field of Search ........................................ 548/453

(56) References Cited

U.S. PATENT DOCUMENTS

| | | | |
|---|---|---|---|
| 5,495,029 A | 2/1996 | Steinmann et al. |
| 6,057,460 A | 5/2000 | Moszner et al. |
| 6,150,479 A | 11/2000 | Klemarczyk et al. |
| 2002/0013420 A1 | 1/2002 | Wang et al. |

FOREIGN PATENT DOCUMENTS

| WO | WO 00/10974 A3 | 3/2000 |
|---|---|---|
| WO | WO 00/10974 A2 | 3/2000 |

OTHER PUBLICATIONS

Crivello, James V. et al.: "Efficient Isomerization of Allyl Ethers and Related Compounds Using Pentacarbonyliron"; The Journal of Organic Chemistry; vol. 63, No. 19, pp. 6745–6748, 1998.

Morel, F. et al.: "Kinetic study of the photo–induced copolymerization of N–substituted maleimides with electron donor monomers"; Polymer 40 (1999) 2447–2454; Elsevier.

Jones, Richard G. et al.: "Facile synthesis of epoxystyrene and its copolymerisations with styrene by living free radical and atom transfer radical strategies"; Polymer 40 (1999) 2411–2418; Elsevier.

Crivello, James V. et al.: "Benzyl Alcohols as Accelerators in the Photoinitiated Cationic Polymerization of Epoxide Monomers"; Journal of Polymer Science: Part A: Polymer Chem., vol. 40, 2298–2309 (2002), 2002 Wiley Periodicals, Inc.

Li, Haiying et al.: "Syntheses and Characterizations of Thermally Degradable Epoxy Resins. III"; J. of Polymer Sci: Part A: Polymer Chemistry, vol. 40, 1796–1807 (2002), 2002 Wiley Periodicals, Inc.

Teng, G. et al.: "Synthesis and characterization of cycloaliphatic diepoxide crosslinkable core–shell latexes"; Polymer 42 (2001) 2849–2862; Elsevier.

Oyama, Toshiyuki et al.: "Photo–crosslinking of polystyrenes having pendant epoxy groups"; Reactive & Functional Polymers 49 (2001) 99–116; Elsevier.

Crivello, James V. et al.: "The Synthesis and Cationic Photopolymerization of Monomers Based on Dicyclopentadiene"; Jnl. Of Polymer Science, Part A: Polymer Chemistry, vol. 37, 3427–3440 (1999), 1999 John Wiley & Sons, Inc.

Xie, Meiran, et al.: "Synthesis and Properties of a Novel, Liquid, Trifunctional, Cycloaliphatic Epoxide"; Jnl. Of Polymer Science, Part A: Polymer Chemistry, vol. 39. 2799–2804 (2001); 2001 John Wiley & Sons, Inc.

Chantarasiri, Nuanphun et al.: "Thermally stable metal–containing epoxy polymers from an epoxy resin–Schiff base metal complex–maleic anhydride system"; European Polymer Journal 37 (2001) 2031–2038; Elsevier.

Crivello, James V. et al.: "Synthesis of Epoxy Monomers That Undergo Synergistic Photopolymerization by a Radical–Induced Cationic Mechanism"; Journal of Polymer Science: Part A, Polymer Chemistry, vol. 39. 3578–3592 (2001), 2001 John Wiley & Sons, Inc.

Konno, Yousuke et al.: "Synthesis of New Photoresponsive Polyesters Containing Norbornadiene Residues by the Polyaddition of Donor–Acceptor Norbornadiene Dicarboxylic Acid Digylcidyl Ester with Dicarboxylic Acids and Their Photochemical Properties"; Journal of Polymer Science: Part A, Polymer Chemistry, vol. 39, 2683–2690 (2001); 2001 John Wiley & Sons, Inc.

Crivello, J. V. et al.: "Synthesis, Characterization, and Polymerization of Propenyl Ether Analogues"; Jnl. Of Polymer Science, Part A, Polymer Chemistry, vol. 32, 2895–2909 (1994), 1994 John Wiley & Sons, Inc.

(List continued on next page.)

Primary Examiner—Taofiq Solola
(74) Attorney, Agent, or Firm—Jane E. Gennaro

(57) ABSTRACT

A curable composition comprises a compound having at least one epoxy group and at least one maleimide, styrenic or cinnamyl group per molecule. A representative compound has the structure

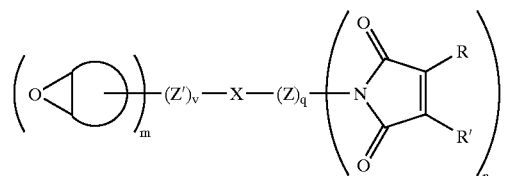

in which Z' and Z are any monomeric, oligomeric or polymeric organic moiety; X is a direct bond or a functional group; and R and R' are hydrogen, an alkyl group having 1 to 12 carbon atoms, or an aromatic or heteroaromatic ring or fused ring having 3 to 10 carbon atoms within the ring structure.

15 Claims, No Drawings

OTHER PUBLICATIONS

Trumbo, D. L. et al.: "Copolymerization Behavior of 3–Isopropenyl–α, α–Dimethylbenzylamine and a Preliminary Evaluation of the Copolymers in Thermoset Coatings"; Jnl. Of Applied Polymer Science, vol. 82, 1030–1039 (2001); 2001 John Wiley & Sons, Inc.

Fujishiro, Koichi et al.: "Thermosetting aromatic episulfide polymers with reduced thermal expansion and water absorption"; Jpn. Kokai Tokkyo Koho JP 2001, 131,286, May 15, 2001, Appl. 1999/318,540, Nov. 9, 1999; 9 pp.

Tomoi, Masao et al.: "Unsaturated epoxy compounds, production method thereof, and photo–crosslinkable (co)polymers therefrom"; Jpn. Kokai Tokkyo Koho JP 2000 290,272, Oct. 17, 2000, Appl. 1999/101,782, Apr. 8, 1999, 7 pp.

Tomoi, Masao et al.: Unsaturated epoxides, their manufacture, and (co)polymers; Jpn. Kokai Tokkyo Koho JP 2000 297,082, Oct. 24, 2000, Appl. 1999/105,799, Apr. 13, 1999; 8 pp.

CYCLOALIPHATIC EPOXY COMPOUNDS CONTAINING STYRENIC, CINNAMYL, OR MALEIMIDE FUNCTIONALITY

FIELD OF THE INVENTION

This invention relates to curable compounds that have a cycloaliphatic epoxy moiety and a styrenic, cinnamyl, or maleimide moiety.

BACKGROUND OF THE INVENTION

Radical-curable compositions are used in adhesive compositions, for example, in the fabrication and assembly of semiconductor packages and microelectronic devices. There are a number of electron donor/electron acceptor adhesive systems that are used in the industry, but not all these give as full performance as is needed for all uses. There are also adhesive systems that contain both radical-curable moieties and epoxy functionality. The compounds disclosed in this specification add to the spectrum of performance materials for use within the semiconductor fabrication industry.

SUMMARY OF THE INVENTION

This invention relates to compounds that have a cycloaliphatic epoxy moiety and an electron acceptor moiety or an electron donor moiety. The preferred electron acceptor is a maleimide moiety. The preferred electron donor is a double bond connected to an aromatic ring and conjugated with the unsaturation in the ring. Preferred electron donor moieties are styrenic or cinnamyl moieties. In another embodiment, this invention is a curable composition, such as an adhesive, coating, or encapsulant composition, containing such compounds.

DETAILED DESCRIPTION OF THE INVENTION

The inventive compounds can be represented by the formulas (in which the bond represented as a wavy line indicates a cis or trans isomer or a racemic mixture of the compound):

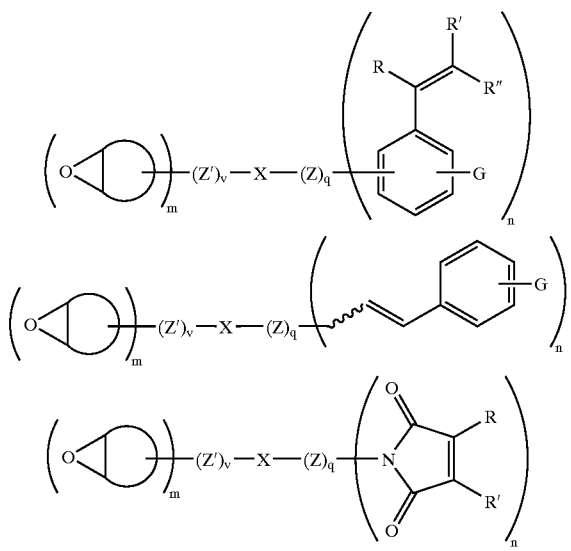

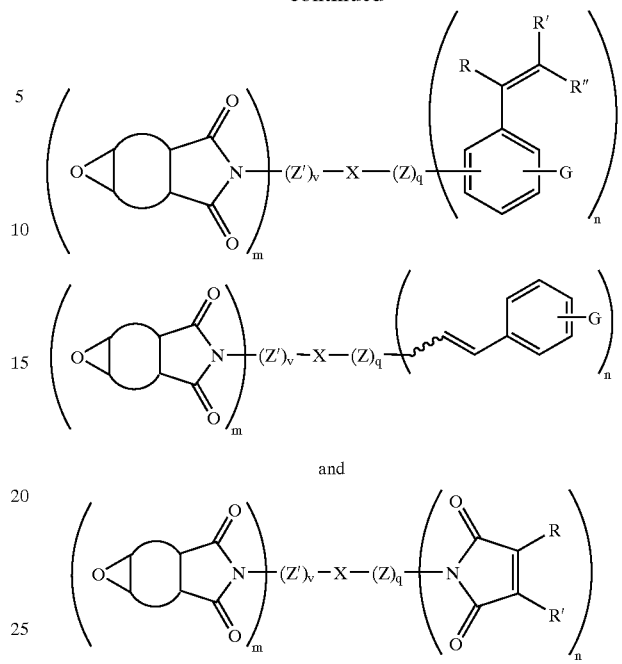

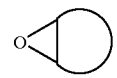

represents a cycloaliphatic epoxy moiety, in which an epoxy group is fused to a cyclic, bicycle or tricyclic ring structure, which structure may contain one or more heteroatoms (N, O, or S); preferably, the cycloaliphatic epoxy moiety is chosen from substituted and unsubstituted five and six membered cyclic rings; substituted and unsubstituted six, seven and eight member bicyclic rings; substituted and unsubstituted nine, ten and eleven member tricyclic rings, in which the substituents on the rings can be any organic moiety, and preferably are lower alkyl;

R, R', and R" are independently hydrogen, an alkyl group having 1 to 12 carbon atoms and preferably H or 1 to 4 carbon atoms, or an aromatic or heteroaromatic ring or fused ring having 3 to 10 carbon atoms within the ring structure, in which the heteroatoms are N, O, or S;

G is —OR, —SR, or —N(R)(R') in which R and R' are as described above; or G is an alkyl group having 1 to 12 carbon atoms; or G is an aromatic or heteroaromatic ring or fused ring having 3 to 10 carbon atoms within the ring structure, in which the heteroatoms may be N, O, or S;

Z and Z' are any monomeric, oligomeric or polymeric organic moiety (for example, alkyl, cycloalkyl, aryl alkyl alkenyl, cycloalkenyl, aryl alkenyl, or aromatic, and for example poly(butadiene), polyether, polyester, polyurethane, polyacrylic, polystyrene, polycarbonate, polysulfone); and X is a direct bond or a functional group selected from the groups consisting of:

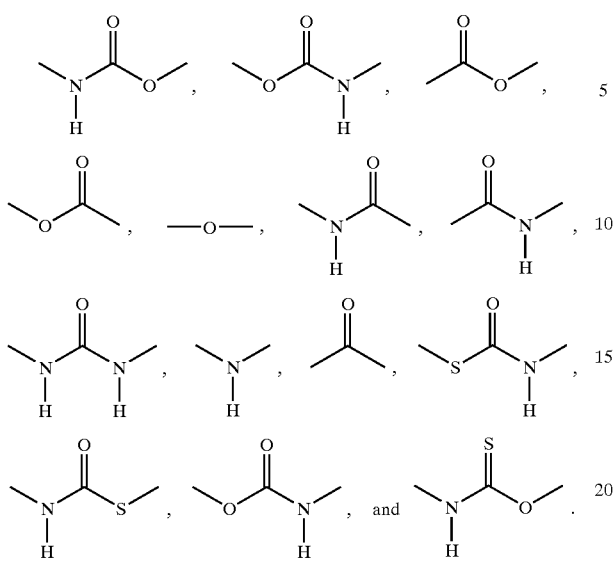

provided that X cannot be oxygen when the cyclic epoxy is epoxy cyclohexane and the other functionality is a styrenic moiety.

Exemplary structures with the cyclic epoxy moieties depicted for such compounds, in which E represents the styrenic, cinnamyl, or maleimide moiety; X, Z, and Z' are as above and R and R' are hydrogen or lower alkyl, and q and v independently are 0 or 1, include:

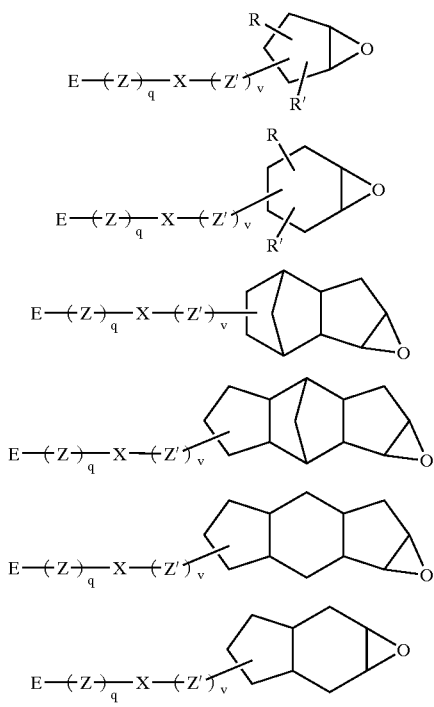

and

-continued

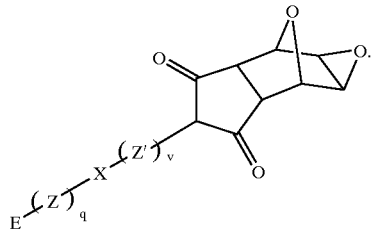

In another embodiment, this invention is a curable composition, such as an adhesive, coating, or encapsulant, containing the compound with both cycloaliphatic epoxy and styrenic, cinnamyl, or maleimide functionality. The composition can be a paste, prepared by blending or milling, or can be a film, prepared by standard film making techniques known to those skilled in the art The curable composition will include optionally a curing agent, and optionally a filler.

These compounds can be the main component in the curable composition or can be added as an adhesion promoter to one or more other curable resins. When used as an adhesion promoter, the amount used in the curable composition will be an effective amount to promote adhesion and, in general, an effective amount will range from 0.005 to 20.0 percent by weight of the formulation.

Examples of other curable resins for use as the main component in the curable compositions include epoxies, vinyl ethers, thiolenes, compounds derived from cinnamyl and styrenic starting compounds, fumarates, maleates, acrylates, and maleimides.

Suitable curing agents are thermal initiators and photoinitiators present in an effective amount to cure the composition. In general, those amounts will range from 0.1% to 30%, preferably 1% to 20%, by weight of the total organic material (that is, excluding any inorganic fillers) in the composition. Preferred thermal initiators include peroxides, such as butyl peroctoates and dicumyl peroxide, and azo compounds, such as 2,2'-azobis(2-methyl-propanenitrile) and 2,2'-azobis(2-methyl-butanenitrile). A preferred series of photoinitiators are those sold under the trademark Irgacure or Rhodorsil 2074 by Ciba Specialty Chemicals. In some formulations, both thermal initiation and photoinitiation may be desirable: the curing process can be started either by irradiation, followed by heat, or can be started by heat, followed by irradiation.

In general, the curable compositions will cure within a temperature range of 60° C. to 250° C., and curing will be effected within a range of three seconds to three hours. The actual cure profile will vary with the components and can be determined without undue experimentation by the practitioner.

The curable compositions may also comprise nonconductive or thermally or electrically conductive fillers. Suitable conductive fillers are carbon black, graphite, gold, silver, copper, platinum, palladium, nickel, aluminum, silicon carbide, boron nitride, diamond, and alumina. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, triflouroethylene, vinylidene fluoride, vinyl fluoride, vinylidene chloride, and vinyl chloride. If present, fillers generally will be in amounts of 20% to 90% by weight of the formulation.

In another embodiment, this invention is a curable composition comprising the compound having a cycloaliphatic epoxy moiety and a styrenic, cinnamyl, or maleimide moiety, and an aliphatic or aromatic epoxy resin. In a preferred embodiment, the epoxy resin has the structure

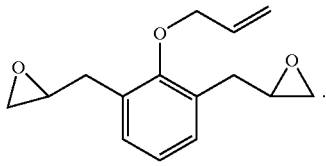

The following Procedures and Examples disclose representative compounds having at least one cycloaliphatic epoxy moiety and one styrenic, cinnamyl, or maleimide moiety per molecule and the synthetic procedures for making those compounds. Also disclosed is the performance of samples in curable compositions.

PROCEDURE 1: Reaction of isocyanate with alcohol. One mole equivalent of isocyanate is solvated in toluene in a three-necked flask equipped with a mechanical stirrer, addition funnel and nitrogen inlet/outlet The reaction is placed under nitrogen, and a catalytic amount of dibutyltin dilaurate (catalyst) is added with stirring as the solution is heated to 60° C. The addition funnel is charged with one mole equivalent of alcohol dissolved in toluene. This solution is added to the isocyanate solution over ten minutes, and the resulting mixture is heated for an additional three hours at 60° C. After the reaction cools to room temperature, the solvent is removed in vacuo to give the product.

PROCEDURE 2: Reaction of alcohol with acid chloride. One mole equivalent of alcohol and triethylamine are mixed in dry methylene chloride at 0° C. One mole equivalent acid chloride dissolved in dry methylene chloride is carefully added. The mixture is allowed to react for four hours. The solvent is evaporated and the crude product is purified by column chromatography using a gradient of hexane/ethyl acetate to give the product.

PROCEDURE 3: Reaction of alkyl halide with alcohol. One mole equivalent of alcohol, excess amount of 50% NaOH, a catalytic amount of tetrabutyl ammonium hydrogen sulfate; and one mole equivalent of alkyl halide in toluene are stirred for five hours at 53° C., then five hours at 75° C. The reaction cools to room temperature and the organic layer extracted and washed with brine three times. The isolated organic layer is then dried over $MgSO_4$, filtered and the solvent removed in vacuo to give the product.

PROCEDURE 4: Reaction of disiloxane with vinyl epoxy. A round-bottomed flask is charged with one mole equivalent of disiloxane and one mole equivalent of vinyl epoxy resin. The reaction flask is equipped with a magnetic stirrer and a reflux condenser. To this mixture is added a catalytic amount of tris(triphenylphosphine)rhodium(I) chloride, and the reaction mixture is heated to 80–85° C. for six hours. The reaction is followed using gas chromatography by monitoring the disappearance of the starting materials and the appearance of the products. After the completion of the reaction, pure product is obtained by fractional vacuum distillation.

PROCEDURE 5: Hydrosilation. One mole equivalent of alkene is dissolved in toluene and placed in a two-necked round bottomed flask. One mole equivalent of epoxy siloxane adduct is added to the flask, and the reaction mixture is heated to 60° C. One drop of Karstedt's catalyst is added, and the hydrosilation reactions are obtained by following disappearance of Si—H band at 2117 $cm^{-1}$ in the infrared spectrum. The reaction is over in approximately two to three hours. After cooling, the reaction mixture is poured with stirring into methanol to precipitate the grafted poly (butadiene) polymer. The precipitated product is washed with methanol and dried in vacuo at 60° C. for eight hours.

PROCEDURE 6: Reaction of alcohol with carboxylic acid. Into four neck flask is placed one mole equivalent of (0.4739 mol) carboxylic acid. Also charged is one mole equivalent (0.2256 mol) of alcohol, and catalytic amount of sulfuric acid. Toluene is used to solvate the reaction mixture. At this point, the flask is fitted with a Dean Stark apparatus, mercury thermometer, mechanical stirrer, and nitrogen blanket. The reaction mixture is raised to reflux (110° C.). Reflux is maintained for approximately four hours at which point the condensate trap is emptied to remove collected water, and allowed to refill with fresh distillate. An equal amount of virgin solvent is charged to the flask to maintain a consistent solvent level. Following another 30 minutes of reflux, the trap is again emptied and allowed to refill; again back charging fresh solvent to replace the distillate that is removed. This process is repeated four more times in an effort to drive the maximum amount of water from the system. Following the final 30 minutes of reflux, the oil bath is removed and the reaction shut down. The solvent is evaporated and the crude product is purified by column chromatography using a gradient of hexane/ethyl acetate to give the product.

PROCEDURE 7: Reaction of amine with acid chloride. One equivalent of amine and one equivalent of triethylamine are mixed in dry methylene chloride at 0° C. One equivalent of acid chloride dissolved in dry methylene chloride is carefully added. The mixture is allowed to react for four hours. The solvent is evaporated and the crude product is purified by column chromatography using a gradient of hexane/ethyl acetate to give the product.

PROCEDURE 8: Conversion of alcohol functionality to chloride functionality. The synthetic procedure is conducted according to E. W. Collington and A. I. Meyers, *J. Org. Chem.* 36, 3044 (1971). A stirred mixture of one mole equivalent of alcohol and 1.1 mole equivalent of s-collidine under nitrogen is treated with one equivalent of lithium chloride dissolved in a minimum amount of dry dimethylformamide. On cooling to 0° C., a suspension is formed, which is treated dropwise with 1.1 mole equivalent of methanesulfonyl chloride. Stirring is continued at 0° C. for one to one and one-half hour, after which time the pale yellow reaction mixture is poured over ice-water. The aqueous layer is extracted with cold ether-pentane (1:1) and the combined extracts are washed successively with saturated copper nitrate solution. This is continued until no further intensification of the blue copper solution occurs, indicating complete removal of s-collidine. The organic extracts are dried ($Na_2SO_4$) and concentrated at room temperature, providing a residue of the product.

PROCEDURE 9: Reaction of alkyl halide with amine. One mole equivalent of alkyl halide is solvated in THF in a three neck flask equipped with a mechanical stirrer and addition funnel. The addition funnel is charged with one mole equivalent of amine in THF. This solution is added to the alkyl halide solution over ten minutes at 0° C., and the resulting mixture is stirred for 12 hours at room temperature. The solvent is removed in vacuo and to the resulting mixture is added ether and water. The organic layer is extracted and dried over $MgSO_4$. The solvent is removed in vacuo to give the product.

PROCEDURE 10: Reaction of carboxylic acid with isocyanate. The synthetic procedure is conducted according to T. Nishikubo, E. Takehara, and A. Kameyama, *Polymer Journal*, 25, 421 (1993). A stirred mixture of one mole equivalent of isocyanate and one mole equivalent of carboxylic acid is solvated in toluene in a three-necked flask equipped with a mechanical stirrer and nitrogen inlet/outlet The mixture is heated for two hours at 80° C. After the reaction cools to room temperature, the solvent is removed in vacuo to give the product.

PROCEDURE 11: Reaction of alcohol with vinyl silane. One mole equivalent of alcohol and triethylamine are mixed in dry toluene at 0° C. One mole equivalent of vinyl silane dissolved in toluene is carefully added. The mixture is allowed to react for four hours at room temperature. The solvent is evaporated to give the product.

EXAMPLE I

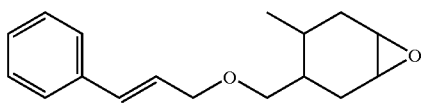

Compound I was prepared from the intermediate methyl cyclohexane methanol epoxide, having the structure

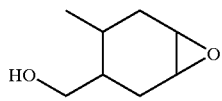

Methyl cychohexane methanol epoxide was prepared as follows: 6-Methyl-3-cyclohexene-1-methanol (50 g, 0.396 mole), a 5% aqueous solution of sodium bicarbonate (63 ml) and dichloromethane (94 ml) were charged to a 1 L 4-necked round-bottom flask equipped with a mechanical stirrer, pH/temperature probe and two 250 ml slow-addition funnels, each with a side-arm. A 40% aqueous solution of potassium hydroxide (250 ml) was charged to funnel #1 and a solution of sodium acetate (10.42 g) dissolved in peracetic acid (32% by weight, 235.4 g total) was charged to funnel #2.

The reaction flask was cooled in an ice bath with vigorous mixing while the peracetic acid solution was added over three hours, maintaining a reaction temperature of 5°–10° C. To maintain the reaction at pH between 6 and 7, potassium hydroxide solution (funnel #1) was added as needed. Following the completion of addition of peracetic acid solution, the reaction temperature was held at 50 to 10° C. for two hours, after which the ice bath was removed.

When the reaction reached room temperature, the pH was raised to 6.5–6.6 with additional potassium hydroxide solution. In this synthesis, the total amount of potassium hydroxide solution added to the reaction was 195 ml. The reaction was then stirred at room temperature for 16 hours.

The organic and aqueous fractions were isolated using a separatory funnel. The product was twice extracted from the aqueous phase with dichloromethane (40 ml each) and the organic fractions were combined and filtered to remove solids. An aqueous sodium bicarbonate solution (5% by weight, 50 ml) was slowly added to the organic fraction and mixed until bubbling stopped. The resulting white emulsion was placed in a separatory funnel and the organic phase was collected. The product was then extracted from the aqueous phase with dichloromethane (25 ml) and the organic phases were combined and filtered.

Next, a 5% aqueous solution of sodium sulfite (190 g) was mixed with a 5% sodium bicarbonate aqueous solution (10 g); this was used in successive portions (20 ml each) to wash the organic fraction. Washing continued until indicator strips measured zero ppm peroxides in the wash solution. The organic phase was dried over anhydrous sodium carbonate (50 g) and filtered. The solvent was removed in vacuo to give the intermediate, methyl cyclohexane methanol epoxide, in 60% yield.

Methyl cyclohexane methanol epoxide (intermediate) (20.00 g, 0.1163 moles), toluene (50 ml), tetrabutyl ammonium hydrogen sulfate (8.70 g, 0.0256 moles) and 50% sodium hydroxide solution (150 ml) were combined in a 500 ml 4-necked round bottom flask equipped with a condenser, mechanical mixer and oil bath. The mixture was stirred and the oil bath was heated to 90° C. at which temperature the solids were totally dissolved.

Cinnamyl chloride was added over approximately 20 minutes. The reaction was heated at 90° C. with mixing for an additional hour and then allowed to cool to room temperature. The organic phase was isolated in a separatory funnel and washed three times with 20% sodium chloride solution (200 ml each). As a result, the pH of the washes dropped from 12 to 6. A final wash (200 ml) using distilled water resulted in an emulsion, which was allowed to separate over night.

After the emulsion separated, a clear bright gold organic fraction was collected and the toluene was stripped in vacuo. The resulting dark orange syrup (approx. 28 g) was dissolved in a solution of hexane and ethyl acetate (100 ml, hexane/ethyl acetate, 2/1 by volume). Silica gel was added to the solution and the mixture was stirred for 30 minutes before filtering out the solids. The solvent was stripped from the solution in vacuo resulting in Compound I as a thin orange liquid in 54% yield.

EXAMPLE II

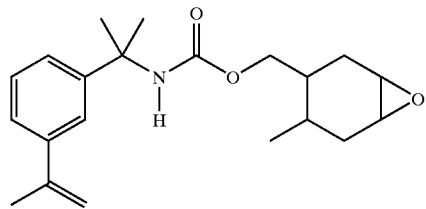

Methyl-cyclohexane epoxide methanol (intermediate from EXAMPLE I) (25 g, 0.1760 moles), 3-isopropenyl-α,α-dimethylbenzyl isocyanate (m-TMI) (35.50 g, 0.1760 moles) and toluene (30 ml) were combined in a 250 ml four-necked round bottom flask equipped with a condenser, mechanical mixer, nitrogen purge and oil bath. The reaction was placed under nitrogen and two drops of dibutyltin dilaurate were added with stirring as the oil bath was heated to 80° C. Heating and stirring of the reaction solution was continued for 24 hours resulting in a clear gold solution. The solvent was removed in vacuo and the product, Compound II, was obtained as thick gold liquid product in quantitative yield.

EXAMPLE III

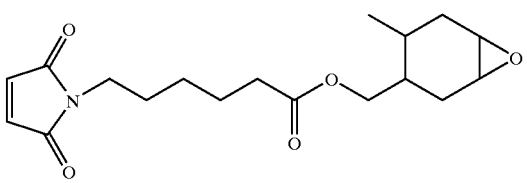

Compound III was prepared from the intermediates 6-maleimidocaproic acid and methyl cyclohexene maleimide.

6-Maleimidocaproic acid, having the structure

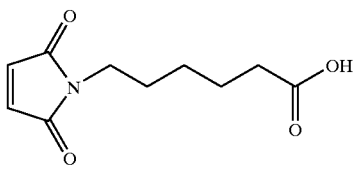

was prepared as follows: A solution of one mole equivalent of maleic anhydride in acetonitrile was added to a one mole equivalent of 6-aminocaprioc acid in acetic acid. The mixture was allowed to react for three hours at room temperature. The formed white crystals were filtered off, washed with cold acetonitrile and dried to produce the amic acid adduct.

The amic acid adduct was mixed with triethylamine in toluene. The mixture was heated to 130° C. for two hours and water was collected in a Dean-Stark trap. The organic solvent was evaporated and 2M HCL added to reach pH 2. Extraction with ethyl acetate and drying over MgSO$_4$ followed by evaporating of the solvent gave the intermediate 6-maleimidocaproic acid (MCA).

The intermediate methyl cyclohexene maleimide, having the structure

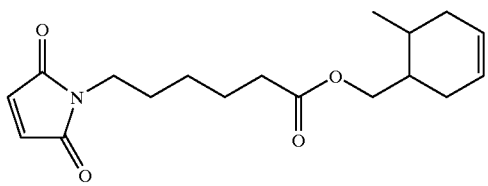

was prepared as follows: 6-maleimidocaproic acid (140.00 g, 0.6635 moles), 6-methyl-3-cyclohexene-1-methanol (69.80 g, 0.5529 mole), and toluene (600 ml) were combined in a 1 L 4-necked round-bottom flask. The flask was fitted with an overhead mixer and thermometer. A Dean-Stark trap was fitted onto the flask with a reflux condenser and nitrogen purge. The mixer and nitrogen purge were started and the oil bath was heated with a set point of 140° C.

When the reaction temperature reached 80° C. the solids dissolved, leaving the reaction mixture a clear copper solution. At this point, sulfuric acid (2.70 g, 0.0276 mole) was added. Reflux was achieved when the oil bath reached approximately 140° C. Refluxing was continued for six hours, during which time the theoretical amount of water (9.95 ml) was collected in the Dean-Stark trap. The trap was emptied and dry toluene (25 ml) was added to the reaction mixture via addition funnel. The replacement of distilled toluene/residual water with dry toluene was repeated three times. The reaction was cooled to 20–25° C. and filtered.

Triethylamine (69.92 g, 0.6910 mole) was added, and the mixture was allowed to stir for one hour. Next, toluene and excess triethylamine were stripped from the reaction solution in vacuo. The resulting amber colored syrup was dissolved in dichloromethane (1000 ml) and this liquid washed with a 20% sodium chloride solution (800 ml). Following separation into two phases, the organic fraction was collected as a gold emulsion. Silica gel (85.00 g) was added to this fraction and the mixture was stirred for 30 minutes. Subsequently, the silica gel was filtered out and the reaction solution was dried over magnesium sulfate. At this point, the reaction was a clear, dark brown solution. The dichloromethane was removed in vacuo, resulting in the intermediate, methyl cyclohexene maleimide as a clear, dark amber syrup in 90% yield.

Methyl cyclohexene maleimide (70.00 g, 0.2295 mole) and dichloromethane (132 g) were charged to a 1 L 4-necked round-bottom flask equipped with a mechanical stirrer, pH/temperature probe and two 250 ml slow-addition funnels, each with a side-arm. A 40% aqueous solution of potassium hydroxide (250 ml) was charged to funnel #1 and a solution of sodium acetate (6.03 g) dissolved in peracetic acid (32% by weight, 137.00 g total) was charged to funnel #2.

The reaction flask was cooled in an ice bath to 5°–10° C. with vigorous mixing and a chilled 5% aqueous solution of sodium bicarbonate (90 ml) was added. Immediately following the addition of the sodium bicarbonate solution, the peracetic acid solution was added slowly while maintaining a reaction temperature of 5°–10°0 C. To maintain the reaction pH between 6 and 7, the potassium hydroxide solution (funnel #1) was added as needed. Following a one and one-half hour addition of the peracetic acid solution, the reaction temperature was held at 5° to 10° C. for two hours and the ice bath was removed.

When the reaction reached room temperature, the pH was raised to 6.5–6.6 with additional 40% potassium hydroxide solution. The reaction was then mixed at room temperature for 16 hours and once again, the pH was raised to 6.4–6.5 with 40% potassium hydroxide solution. In this example, the total amount of 40% potassium hydroxide solution added throughout the reaction was 137 ml.

The organic fraction was isolated using a separatory funnel. Product was then twice extracted from the aqueous phase with dichloromethane (20 ml each). The organic fractions were combined and washed with saturated sodium chloride solution (100 ml) in a separatory funnel. Triethylamine (63.9 g, 0.6312 moles) was added to the hazy gold organic fraction and the color changed to dark orange, immediately. After one hour of mixing, the organic fraction was filtered and washed again with 200 ml saturated sodium chloride solution to remove residual peroxide. Washing continued until indicator strips measured zero ppm peroxides in the wash solution.

Next, toluene (400 ml) was used to extract product from the composite wash solution. Dichloromethane was stripped from the organic fraction in vacuo and the resulting opaque amber syrup was dissolved in more toluene. The toluene fractions were combined and then washed with more saturated sodium chloride solution (300 ml). The organic layer was dried over magnesium sulfate, filtered and stripped in vacuo of toluene and residual triethylamine resulting in Compound III as a cloudy amber syrup in 76% yield.

EXAMPLE IV

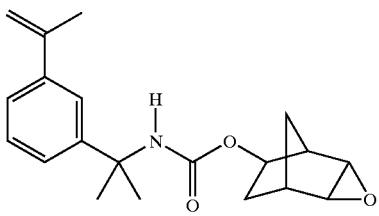

According to the procedure from EXAMPLE I, 5-norbornen-2-ol is reacted with peracetic acid (32% by weight) followed by reaction with M-TMI according to PROCEDURE 1.

EXAMPLE V

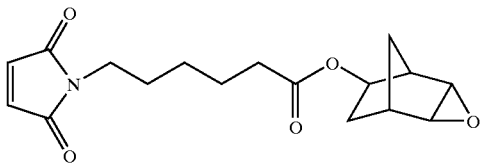

According to PROCEDURE 6, 5-norbornen-2-ol is reacted with 6-maleimidocaproic acid (intermediate from EXAMPLE III), followed by reaction with peracetic acid (32% by weight) according to the procedure from EXAMPLE III.

EXAMPLE VI

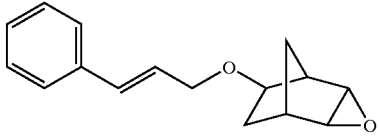

According to the procedure from EXAMPLE I, 5-norbornen-2-ol is reacted with peracetic acid (32% by weight) followed by reaction with cinnamyl chloride according to PROCEDURE 3.

EXAMPLE VII

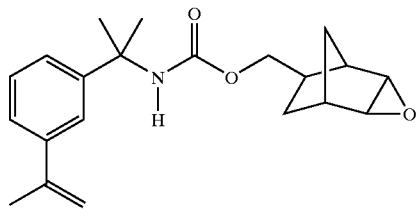

According to the procedure from EXAMPLE I, 5-norbornen-2-methanol is reacted with peracetic acid (32% by weight) followed by reaction with M-TMI according to PROCEDURE 1.

EXAMPLE VIII

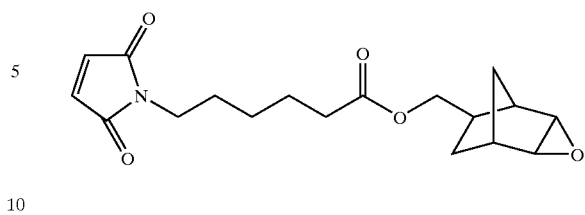

According to PROCEDURE 6, 5-norbornene-2-methanol is reacted with 6-maleimidocaproic acid (intermediate from EXAMPLE III), followed by reaction with peracetic acid (32% by weight) according to the procedure from EXAMPLE III.

EXAMPLE IX

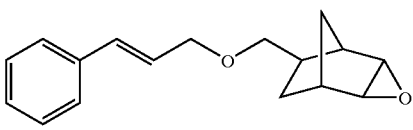

According to the procedure from EXAMPLE I, 5norbornen-2-methanol is reacted with peracetic acid (32% by weight) followed by reaction with cinnamyl chloride according to PROCEDURE 3.

EXAMPLE X

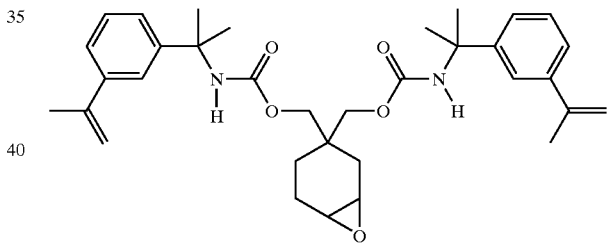

According to the procedure from EXAMPLE I, 3cyclo-hexene-1,1-dimethanol is reacted with peracetic acid (32% by weight) followed by reaction with m-TMI according to PROCEDURE 1.

EXAMPLE XI

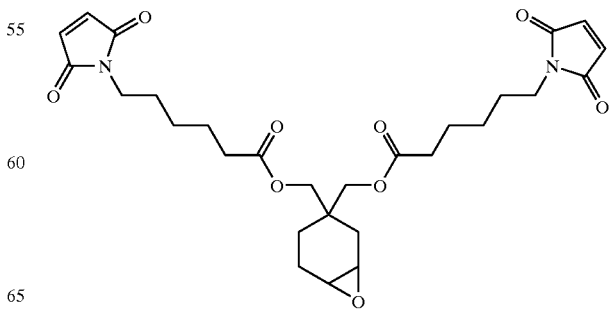

According to PROCEDURE 6, 3-cyclohexene-1,1-dimethanol is reacted with 6-maleimidocaproic acid (intermediate from EXAMPLE III), followed by reaction with peracetic acid (32% by weight) according to the procedure from EXAMPLE III.

EXAMPLE XII

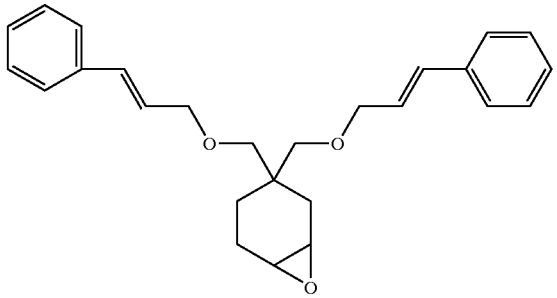

According to the procedure from EXAMPLE I, 3-cyclohexene-1,1-dimethanol is reacted with peracetic acid (32% by weight) followed by reaction with cinnamyl chloride according to PROCEDURE 3.

EXAMPLE XIII

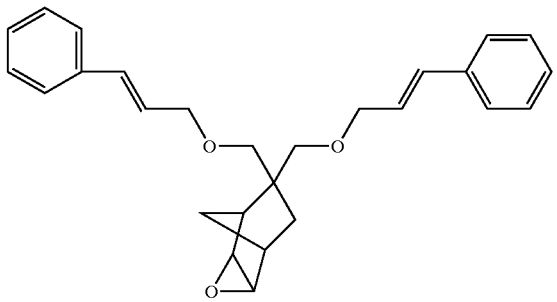

According to the procedure from EXAMPLE I, 5-norbornene-2,2-dimethanol is reacted with peracetic acid (32% by weight) followed by reaction with cinnamyl chloride according to PROCEDURE 3.

EXAMPLE XIV

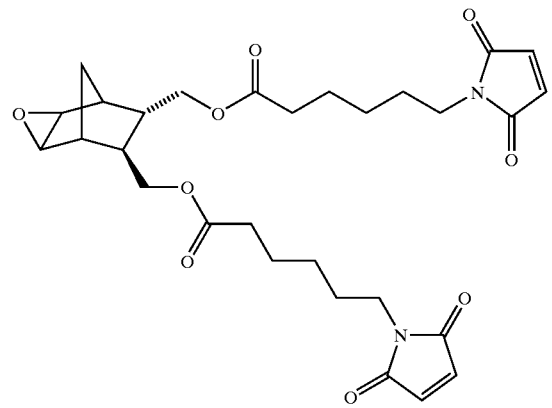

According to PROCEDURE 6, (2-endo;3-exo)-bicyclo[2.2.2]-octa-5-ene-2,3-dimethanol is reacted with 6-maleimidocaproic acid (intermediate from EXAMPLE III), followed by reaction with peracetic acid (32% by weight) according to the procedure from EXAMPLE III.

EXAMPLE XV

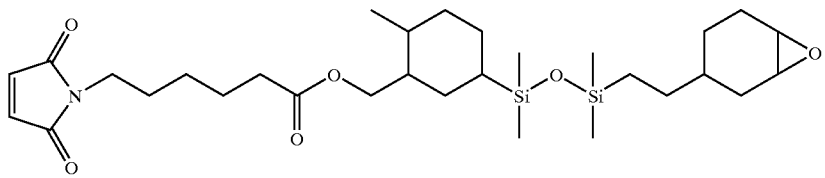

According to PROCEDURE 4, 3-vinyl-7-oxabicyclo[4.1.0]-heptane is reacted with 1,1,3,3-tetramethyldisiloxane to give 1-[2(3[7-oxabicyclo[4.1.0]heptyl])ethyl]-1,1,3,3-tetramethyldisiloxane, further reacted with methyl cyclohexene maleimide from EXAMPLE III according to PROCEDURE 5.

EXAMPLE XVI

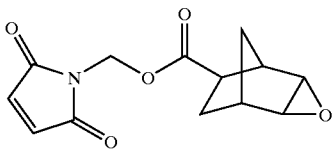

According to PROCEDURE 6, 5-norbornene-2-carboxylic acid is reacted with N-methylolmaleimide (prepared according to J. Bartus, W. L. Simonsick, and O. Vogl, *J.M.S.-Pure Appl. Chem.*, A36(3), 355, 1999), followed by reaction with peracetic acid (32% by weight) according to the procedure from EXAMPLE III.

EXAMPLE XVII

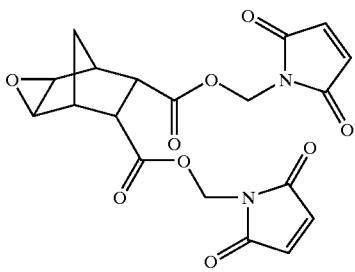

According to PROCEDURE 6, cis-5-norbornene-endo-2,3-dicarboxylic acid is reacted with N-methylolmaleimide (prepared according to J. Bartus, W. L. Simonsick, and O. Vogl, *J.M.S.-Pure Appl. Chem.*, A36(3), 355, 1999), followed by reaction with peracetic acid (32% by weight) according to the procedure from EXAMPLE III.

EXAMPLE XVIII

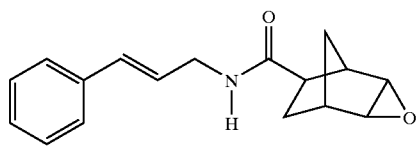

According to the procedure from EXAMPLE I, 5-norbornene-2-acid chloride is reacted with peracetic acid (32% by weight) followed by reaction with cinnamyl amine according to PROCEDURE 7.

EXAMPLE XIX

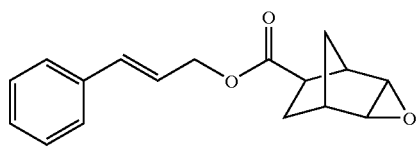

According to the procedure from EXAMPLE I, 5-norbornen-2-acid chloride is reacted with peracetic acid (32% by weight) followed by reaction with cinnamyl alcohol according to PROCEDURE 2.

EXAMPLE XX

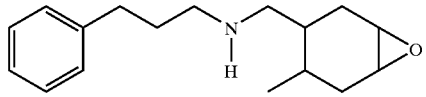

Methyl-cyclohexane epoxide methanol (intermediate from EXAMPLE I) is converted to methyl-cyclohexane epoxide methyl chloride according to PROCEDURE 8, followed by reaction with cinnamyl amine according to PROCEDURE 9.

EXAMPLE XXI

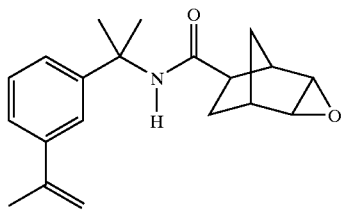

According to the procedure from EXAMPLE I, 5-norbornene-2-carboxylic acid is reacted with peracetic acid (32% by weight) followed by reaction with m-TMI according to PROCEDURE 10.

EXAMPLE XXII

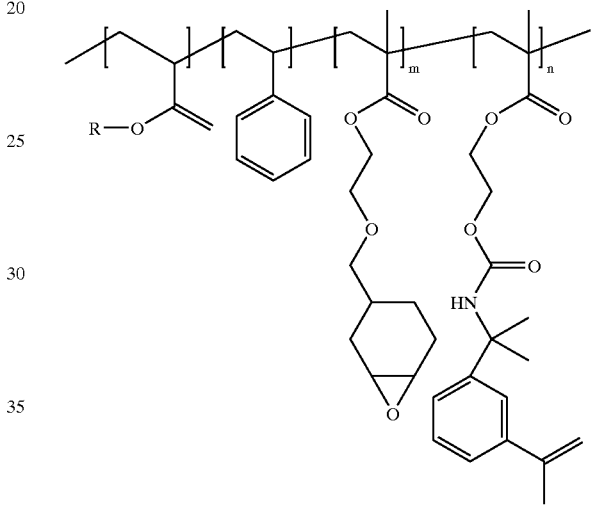

In which n and m are approximately 11 and the molecular weight is approximately 17,000

Methylcyclohexane epoxide methanol (intermediate from EXAMPLE I) is converted to methylcyclohexane epoxide methyl chloride according to PROCEDURE 8, followed by reaction with styrene acrylic polymer (Joncryl 587 from Johnson Polymer) according to PRODECURE 3, followed by reaction with m-TMI according to PROCEDURE 1.

EXAMPLE XXIII

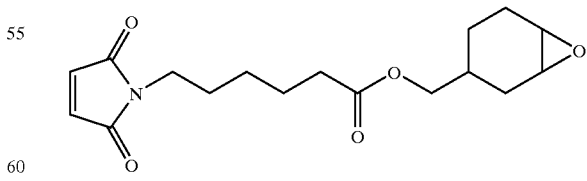

According to PROCEDURE 6, 3-cyclohexene-1-methanol is reacted with 6-maleimidocaproic acid (intermediate from EXAMPLE III), followed by reaction with peracetic acid (32% by weight) according to the procedure from EXAMPLE 3.

EXAMPLE XXIV

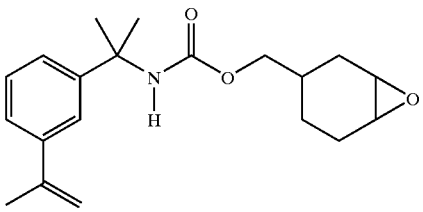

According to the procedure from EXAMPLE I, 3-cyclohexene-1-methanol is reacted with peracetic acid (32% by weight) followed by reaction with m-TMI according to PROCEDURE 1.

EXAMPLE XXV

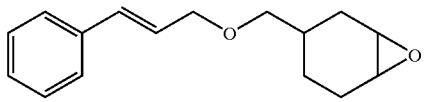

According to the procedure from EXAMPLE I, 3-cyclohexene-1-methanol is reacted with peracetic acid (32% by weight) followed by reaction with cinnamyl chloride according to PROCEDURE 3.

EXAMPLE XXVI

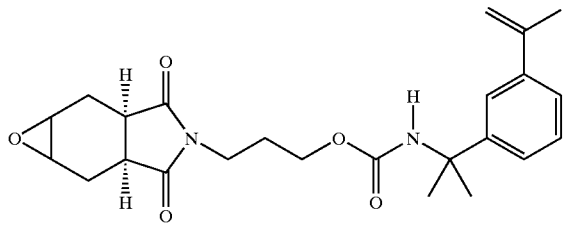

A solution of one mole equivalent of cis-1,2,3,6-tetrahydrophthalic anhydride in acetonitrile is added to a one mole equivalent of propanol amine. The mixture is allowed to react for three hours at room temperature. The formed white crystals are filtered off, washed with cold acetonitrile and dried to produce the amic acid adduct. Amic acid is mixed with triethylamine in toluene. The mixture is heated to 130° C. for two hours and water is collected in a Dean-Stark trap. The organic solvent is evaporated and 2M HCl added to reach pH 2. Extraction with ethyl acetate and drying over MgSO4 followed by evaporation of the solvent gives hydroxy propyl tetrahydrophthalimide. According to the procedure from EXAMPLE I, hydroxy propyl tetrahydro-phthalimide is reacted with peracetic acid (32% by weight) followed by reaction with m-TMI according to PROCEDURE 1.

EXAMPLE XXVII

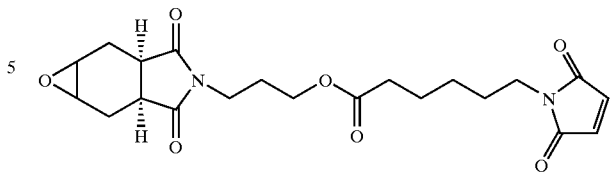

A solution of one mole equivalent of cis-1,2,3,6-tetrahydrophthalic anhydride in acetonitrile is added to a one mole equivalent of propanol amine. The mixture is allowed to react for three hours at room temperature. The formed white crystals are filtered off, washed with cold acetonitrile and dried to produce the amic acid adduct. Amic acid is mixed with triethylamine in toluene. The mixture is heated to 130° C. for two hours and water is collected in a Dean-Stark trap. The organic solvent is evaporated and 2M HCl added to reach pH 2. Extraction with ethyl acetate and drying over MgSO4 followed by evaporation of the solvent gives hydroxy propyl tetrahydrophthalimide. According to PROCEDURE 2, hydroxy propyl tetrahydrophthalimide is reacted with 6-maleimidocaproic acid (intermediate from EXAMPLE III), followed by reaction with peracetic acid (32% by weight) according to the procedure from EXAMPLE III.

EXAMPLE XXVIII

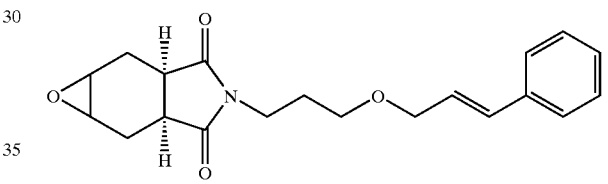

A solution of one mole equivalent of cis-1,2,3,6-tetrahydrophthalic anhydride in acetonitrile is added to a one mole equivalent of propanol amine. The mixture is allowed to react for three hours at room temperature. The formed white crystals are filtered off, washed with cold acetonitrile and dried to produce the amic acid adduct. Amic acid is mixed with triethylamine in toluene. The mixture is heated to 130° C. for two hours and water is collected in a Dean-Stark trap. The organic solvent is evaporated and 2M HCl added to reach pH 2. Extraction with ethyl acetate and drying over MgSO4 followed by evaporation of the solvent gives hydroxy propyl tetrahydrophthalimide. According to the procedure from EXAMPLE I, hydroxy propyl tetrahydrophthalimide is reacted with peracetic acid (32% by weight) followed by reaction with cinnamyl chloride according to PROCEDURE 3.

EXAMPLE XXIX

Performance in adhesive formulation. An adhesive composition was prepared to contain 20 parts by weight of a bismaleimide resin, 5 parts by weight of an acrylate resin, 3 parts by weight of the compound from EXAMPLE II, 0.15 parts by weight of a photoinitiator, 0.4 parts by weight of a radical initiator, and 48.5 parts by weight of silica filler. The formulation was used to adhere a 3×3 mm silicon die to a silver coated copper leadframe. The adhesive was cured by heating at 175° C. for 10 seconds. Die shear strength was measured with a Dage 2400-PC Die Shear Tester at room temperature. Ten samples were tested with the average result being 17 Kg force.

What is claimed is:

1. A compound having the structure:

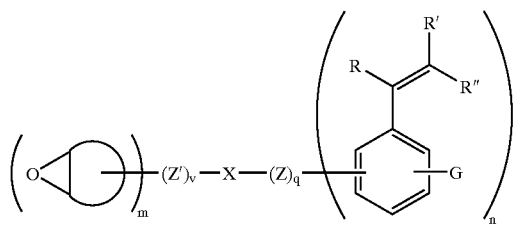

in which
m and n independently are 1 to 500, q and v independently are 0 or 1;

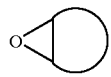

is a cycloaliphatic epoxy moiety, in which an epoxy group is fused to a cyclic, bicyclic or tricyclic ring structure, which structure may contain one or more heteroatoms;

R, R', and R" are independently hydrogen, an alkyl group having 1 to 12 carbon atoms, or an aromatic or heteroaromatic ring or fused ring having 3 to 10 carbon atoms within the ring structure, in which the heteroatoms are N, O, or S;

G is —OR, —SR, or —N(R)(R') in which R and R' are as described above; or

G is an alkyl group having 1 to 12 carbon atoms; or

G is an aromatic or heteroaromatic ring or fused ring having 3 to 10 carbon atoms within the ring structure;

Z and Z' are any monomeric, oligomeric or polymeric organic moiety;

X is a direct bond or a functional group selected from the groups consisting of:

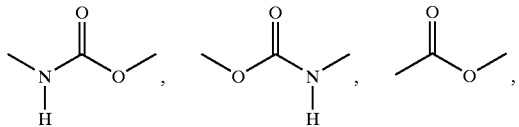

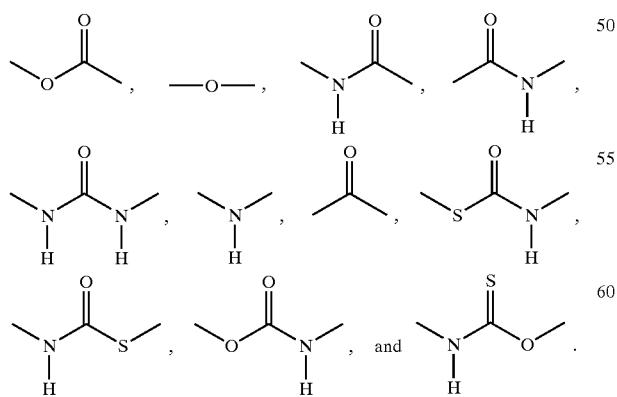

provided that X cannot be oxygen when the cycloaliphatic epoxy moiety is epoxy cyclohexane.

2. The compound according to claim 1 in which the cycloaliphatic epoxy moiety is selected from the group consisting of substituted and unsubstituted five and six membered cyclic rings; substituted and unsubstituted six, seven and eight member bicyclic rings; substituted and unsubstituted nine, ten and eleven member tricyclic rings, in which any substituents on the rings are lower alkyl groups.

3. The compound according to claim 1 selected from the group consisting of

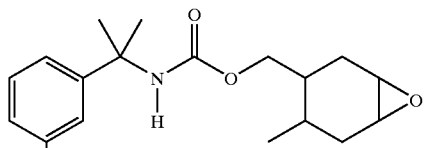

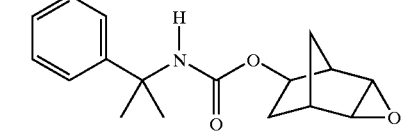

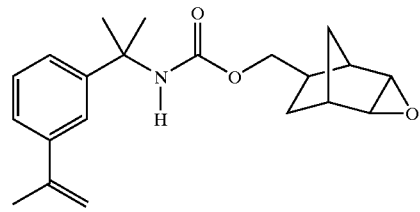

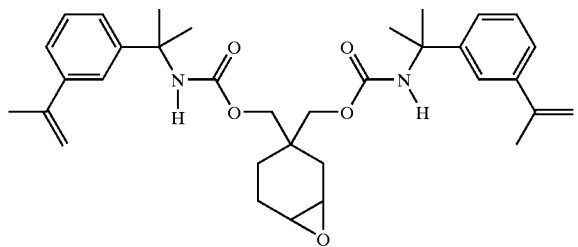

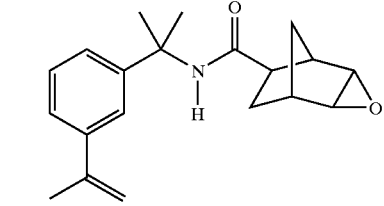

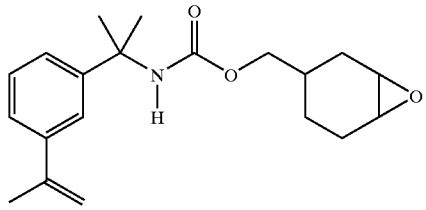

and

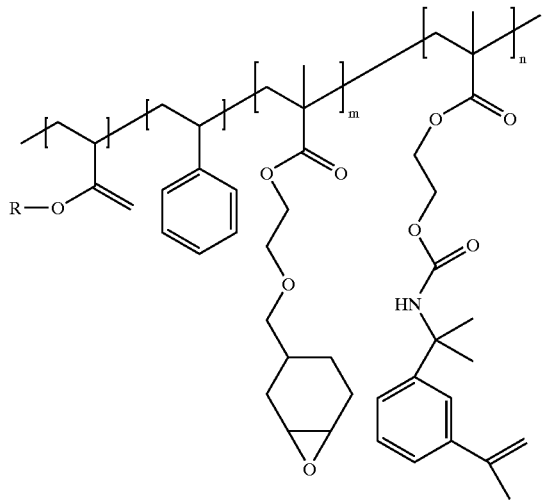

in which n and m are approximately 11, and the molecular weight is approximately 17,000.

4. A compound having the structure

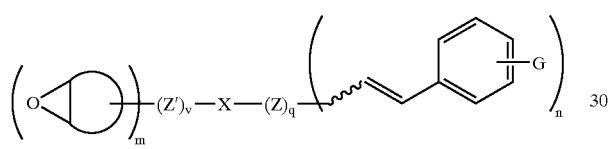

in which m and n independently are 1 to 500, q and v independently are 0 or 1;

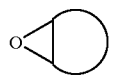

is a cycloaliphatic epoxy moiety, in which an epoxy group is fused to a cyclic, bicyclic or tricyclic ring structure, which structure may contain one or more heteroatoms;

G is —OR, —SR, or —N(R)(R') in which R and R' are independently hydrogen, an alkyl group having 1 to 12 carbon atoms, or an aromatic or heteroaromatic ring or fused ring having 3 to 10 carbon atoms within the ring structure; or G is an alkyl group having 1 to 12 carbon atoms; or G is an aromatic or heteroaromatic ring or fused ring having 3 to 10 carbon atoms within the ring structure;

Z and Z' are any monomeric, oligomeric or polymeric organic moiety;

X is a direct bond or a functional group selected from the groups consisting of:

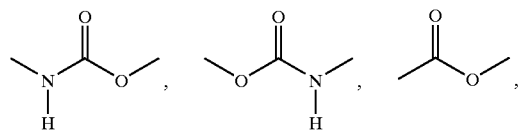

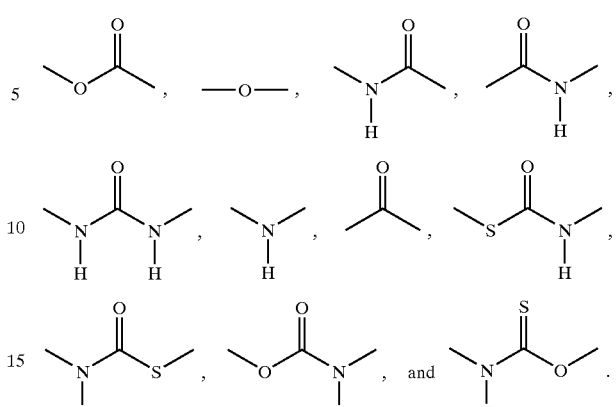

5. The compound according to claim 4 in which the cycloaliphatic epoxy moiety is selected from the group consisting of substituted and unsubstituted five and six membered cyclic rings; substituted and unsubstituted six, seven and eight member bicyclic rings; substituted and unsubstituted nine, ten and eleven member tricyclic rings, in which any substituents on the rings are lower alkyl groups.

6. Compound according to claim 4 selected from the group consisting

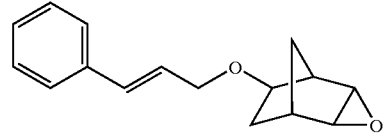

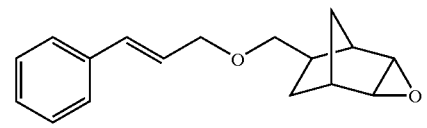

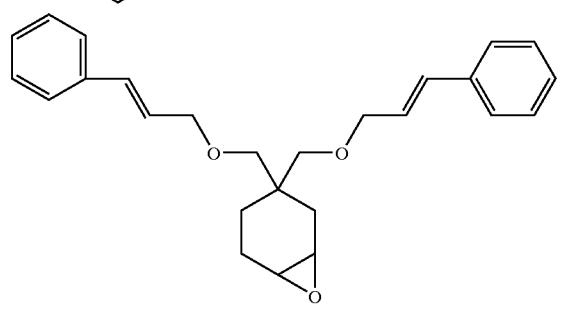

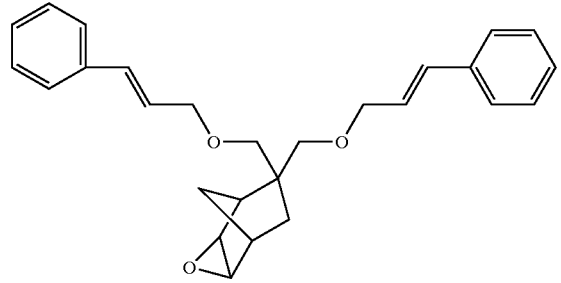

-continued

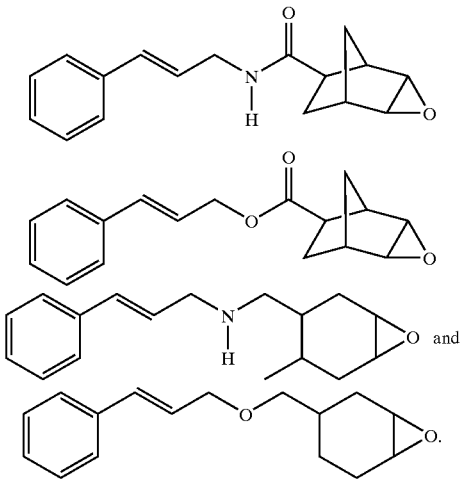

7. A compound having the structure

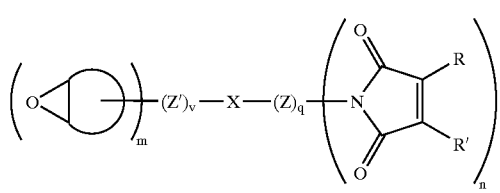

in which m and n independently are 1 to 500, q and v independently are 0 or 1;

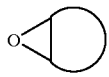

is a cycloaliphatic epoxy moiety, in which an epoxy group is fused to a cyclic, bicyclic or tricyclic ring structure, which structure may contain one or more heteroatoms;

R, and R' independently are hydrogen, an alkyl group having 1 to 12 carbon atoms, or an aromatic or heteroaromatic ring or fused ring having 3 to 10 carbon atoms within the ring structure;

Z and Z' are any monomeric, oligomeric or polymeric organic moiety;

X is a direct bond or a functional group selected from the groups consisting of:

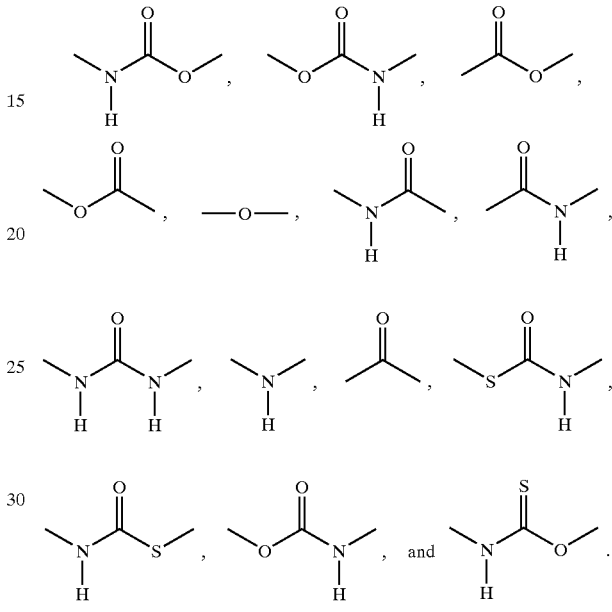

8. The compound according to claim 7 in which the cycloaliphatic epoxy moiety is selected from the group consisting of substituted and unsubstituted five and six membered cyclic rings; substituted and unsubstituted six, seven and eight member bicyclic rings; substituted and unsubstituted nine, ten and eleven member tricyclic rings, in which any substituents on the rings are lower alkyl groups.

9. The compound according to claim 7 selected from the group consisting of

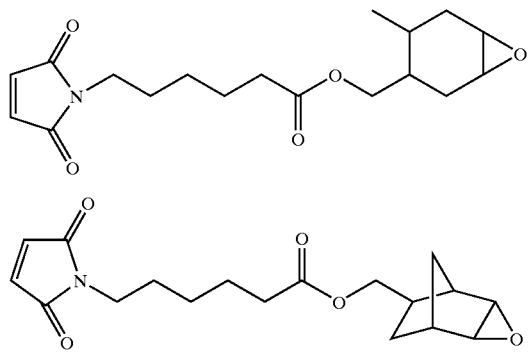

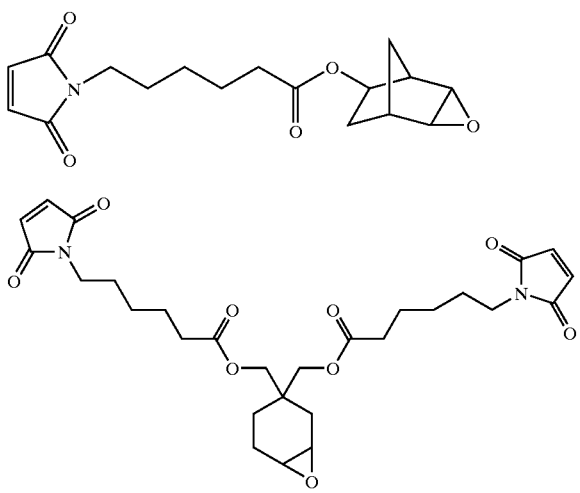

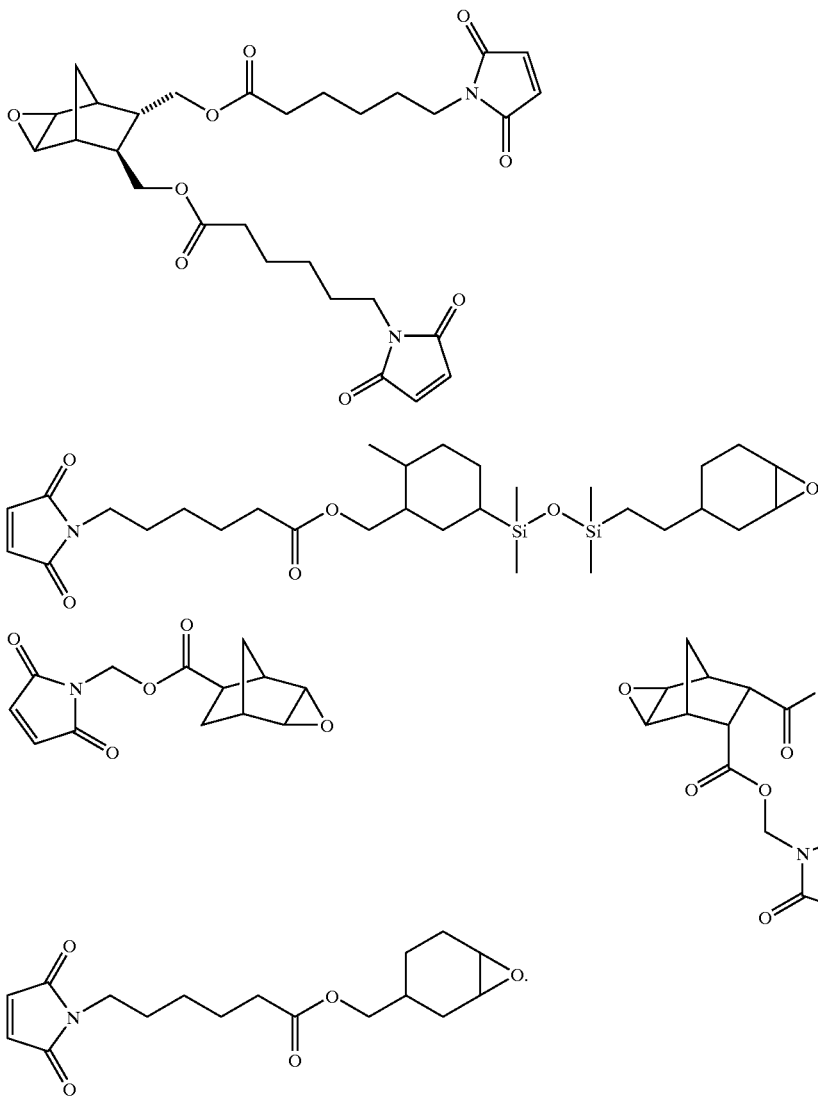

10. A compound having the structure:

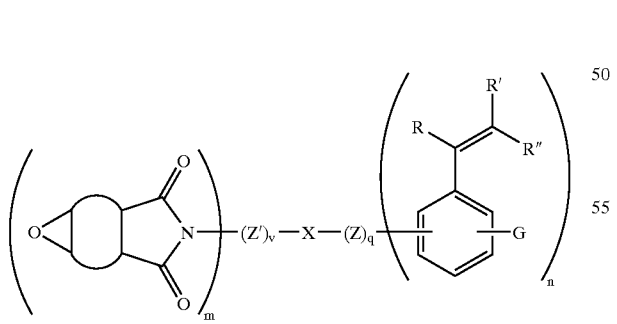

in which m and n independently are 1 to 500, q and v independently are 0 or 1;

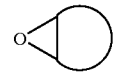

is a cycloaliphatic epoxy moiety, in which an epoxy group is fused to a cyclic, bicyclic or tricyclic ring structure, which structure may contain one or more heteroatoms;

R, R', and R" are independently hydrogen, an alkyl group having 1 to 12 carbon atoms, or an aromatic or heteroaromatic ring or fused ring having 3 to 10 carbon atoms within the ring structure;

G is —OR, —SR, or —N(R)(R') in which R and R' are as described above; or G is an alkyl group having 1 to 12 carbon atoms; or G is an aromatic or heteroaromatic ring or fused ring having 3 to 10 carbon atoms within the ring;

Z and Z' are any monomeric, oligomeric or polymeric organic moiety;

X is a direct bond or a functional group selected from the groups consisting of:

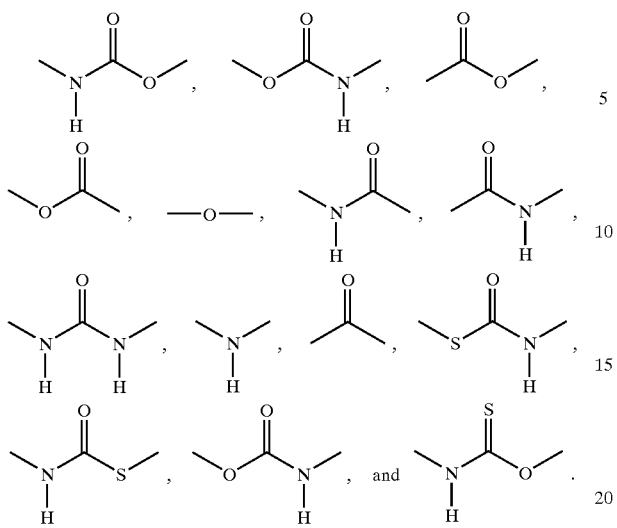

11. The compound according to claim 10 having the structure:

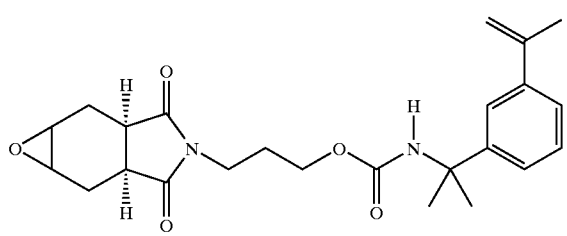

12. A compound having the structure:

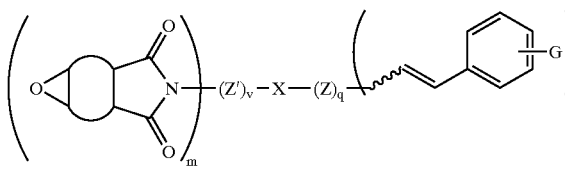

in which
m and n independently are 1 to 500, q and v independently are 0 or 1;

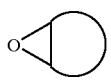

is a cycloaliphatic epoxy moiety, in which an epoxy group is fused to a cyclic, bicyclic or tricyclic ring structure, which structure may contain one or more heteroatoms;
G is —OR, —SR, or —N(R)(R') in which R and R' are independently hydrogen, an alkyl group having 1 to 12 carbon atoms, or an aromatic or heteroaromatic ring or fused ring having 3 to 10 carbon atoms within the ring structure; or
G is an alkyl group having 1 to 12 carbon atoms; or
G is an aromatic or heteroaromatic ring or fused ring having 3 to 10 carbon atoms within the ring structure;
Z and Z' are any monomeric, oligomeric or polymeric organic moiety;

X is a direct bond or a functional group selected from the groups consisting of:

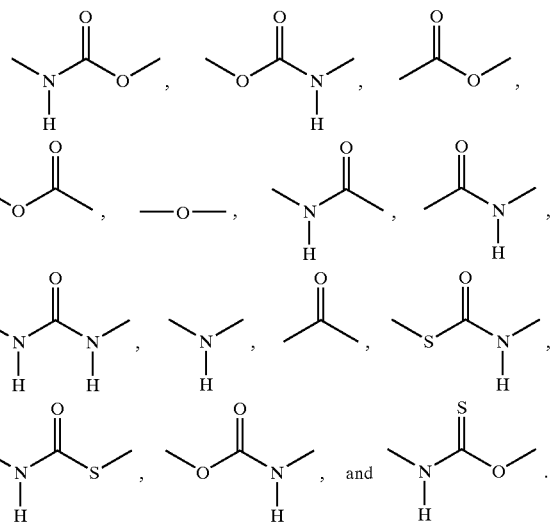

13. The compound according to claim 12 having the structure

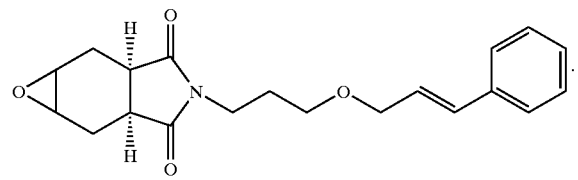

14. A compound having the structure:

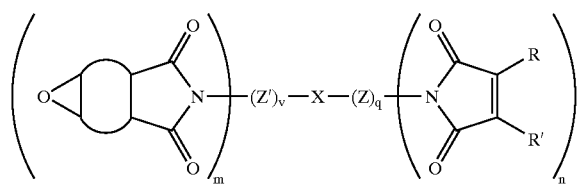

in which
m and n independently are 1 to 500, q and v independently are 0 or 1;

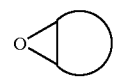

is a cycloaliphatic epoxy moiety, in which an epoxy group is fused to a cyclic, bicyclic or tricyclic ring structure, which structure may contain one or more heteroatoms;
R and R' are independently hydrogen, an alkyl group having 1 to 12 carbon atoms, or an aromatic or heteroaromatic ring or fused ring having 3 to 10 carbon atoms within the ring structure;
Z and Z' are any monomeric, oligomeric or polymeric organic moiety;
X is a direct bond or a functional group selected from the groups consisting of:

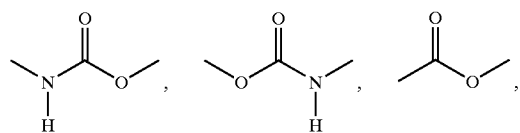
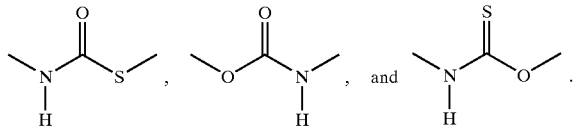
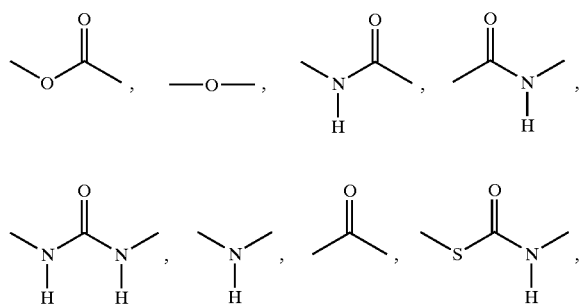
15. The compound according to claim 14 having the structure
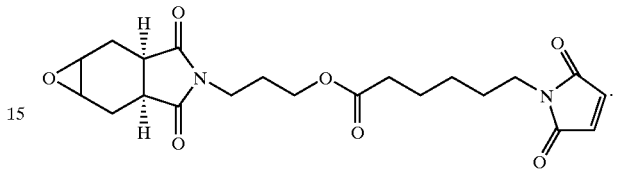
* * * * *